United States Patent

Brumfield et al.

Patent Number: 5,352,231
Date of Patent: Oct. 4, 1994

[54] NUT STARTER WRENCH FOR ORTHOPEDIC FIXATION SYSTEM

[75] Inventors: David L. Brumfield, Southaven, Miss.; Robert A. Farris, Memphis, Tenn.

[73] Assignee: Danek Medical, Inc., Memphis, Tenn.

[21] Appl. No.: 980,554

[22] Filed: Nov. 23, 1992

[51] Int. Cl.⁵ .............................................. A61F 2/32
[52] U.S. Cl. ................................. 606/99; 606/104
[58] Field of Search ................................. 606/62–73, 606/86–91, 99, 100, 104

[56] References Cited

U.S. PATENT DOCUMENTS

| | | | |
|---|---|---|---|
| 1,677,473 | 7/1928 | Gast | 81/55 |
| 2,574,352 | 11/1951 | Serter | 81/125 |
| 2,632,351 | 3/1953 | Hannah | 81/125 |
| 3,334,624 | 8/1967 | Schneider | 606/100 |
| 3,630,107 | 12/1971 | Carr | 81/125 |
| 3,789,705 | 2/1974 | Naslund | 81/13 |
| 3,889,558 | 6/1975 | Duncan | 81/55 |
| 3,892,232 | 7/1975 | Neufeld | 128/92 |
| 4,229,999 | 10/1980 | Rottigni | 91/3 F |
| 4,616,638 | 10/1986 | Griggs | 128/92 BB |
| 4,716,894 | 1/1988 | Lazzeri et al. | 128/92 V |
| 4,744,273 | 5/1988 | Burtok | 81/125 |
| 4,963,144 | 10/1990 | Huene | 606/73 |

Primary Examiner—Michael A. Brown
Attorney, Agent, or Firm—Woodard, Emhardt, Naughton, Moriarty & McNett

[57] ABSTRACT

A tool assembly has a shaft with a sleeve slidable along it. A hexagonal drive post at the lower end of tile shaft is received in a hex socket at the upper end of a bone bolt secured in a patient's spine. A nut to secure a connector on the bolt, is temporarily stored on a short thread on the shaft near the lower end. The sleeve is slid down the shaft and a hex socket at tile lower end of tile sleeve is received on the nut. The sleeve is manually turned while a handle on a drive post at the top of the shaft prevents the shaft, and thereby the bolt, from turning. As the sleeve turns, the nut is turned off the short thread and down onto the bolt thread. A torque wrench coupled to a tool receiving surface at the top of the sleeve tightens the nut on the bolt to the specified torque while the handle on the top of the shaft prevents the bolt from turning.

19 Claims, 4 Drawing Sheets

NUT STARTER WRENCH FOR ORTHOPEDIC FIXATION SYSTEM

BACKGROUND OF THE INVENTION

1. Field of the Invention

This invention relates generally to spinal fixation devices, and more particularly to a wrench for facilitating the mounting and tightening of a nut onto a bolt secured in a bone of a person's spine.

2. Description of the Prior Art

During the application of spinal fixation devices to the spine of a person, there is often some difficulty in the assembly of a nut onto a bolt which is deeply implanted in the person's spine, particularly in the pedicle. The surgical exposure to a patient's lumbar spine is very deep, meaning that there is typically four to five inches of skin and muscle tissue against which instruments have to be used. It is often necessary to attach nuts to bolts that are screwed into the pedicle. Because the nuts are comparatively small, and the depth in tissue is significant, it is usually difficult to properly align a nut with the thread on the bolt to get the nut started. Another problem after the nut has been mounted on the bolt, is to avoid tightening of the nut so much as to cause the bolt to turn in the bone, which would result either in advancing the bolt farther into the bone than is intended, or the strippage of the bone screw threads of the bolt in the patient's spine pedicle. The present invention is directed to avoiding these problems.

SUMMARY OF THE INVENTION

Described briefly, according to a typical embodiment of the present invention, a tool assembly is used which includes a shaft, sleeve, control handle and torque wrench. The shaft has a small drive post at a lower end for reception into a mating drive socket at the upper end of a bone fixation bolt. The upper end of the shaft has a drive post configuration for reception in a mating adaptor or quick-connect coupler for engagement with the control handle or a torque wrench. A short thread is provided on the shaft to receive and temporarily store the nut which is to be installed onto the bone bolt.

The sleeve portion of the tool assembly is received and guided on the shaft and has a socket at tile lower end of the sleeve which is sized to fit the stored nut, for driving the nut off the thread of the shaft and onto the bolt. The upper end of the sleeve has an external, tool receiving surface thereon for mating with a torque wrench coupler for final tightening of the nut on the bolt while the bolt is prevented from turning by holding the control handle on the top of the shaft. The sleeve also has an internal square drive socket for the alternate use of a self-limiting torque wrench if, in a given case, the surgeon is confident that the control handle and shaft are not needed to prevent the bone bolt from turning in the bone.

In order to install a nut on a bone bolt, the sleeve is mounted on the shaft and the handle is attached to the upper end of the shaft. The nut is threaded onto the short length of thread. Then the shaft is placed in the installation site with the small drive post received in the drive socket at the upper end of the bolt. Then the socket sleeve park of the tool assembly is slid down on the shaft and the lower end socket in the sleeve is installed on the nut. Then the socket is manually rotated and moved downward. As it does so, the nut is screwed off the short thread and guided onto the external thread of the bone bolt. After the nut has been tightened to the point where it is snug, the torque wrench is coupled to the upper end of the sleeve and, while the shaft is held against turning by the surgeon holding the handle, the nut is tightened to the desired torque by the surgeon applying the torque wrench with the other hand until the desired tightening torque on the nut is reached.

DESCRIPTION OF THE PREFERRED EMBODIMENT

Figure 1:
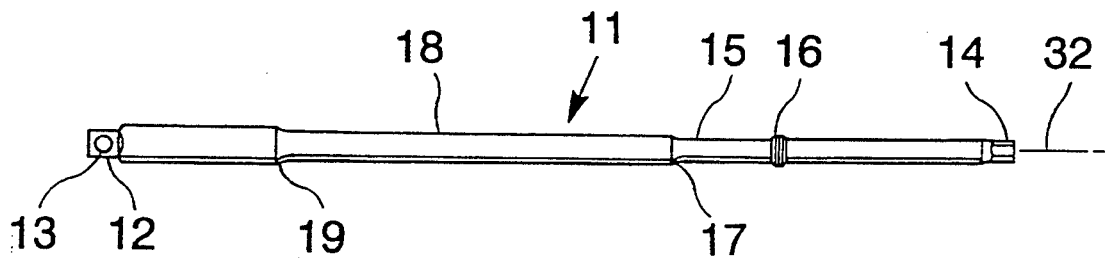
FIG. 1 is a side elevational view of the shaft portion of the nut starter wrench assembly according to a typical embodiment of the present invention.
Figure 2:
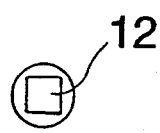
FIG. 2 is a left-hand end view thereof.
Figure 3:
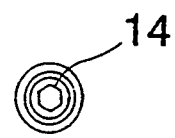
FIG. 3 is a right-hand end view thereof.
Figure 4:
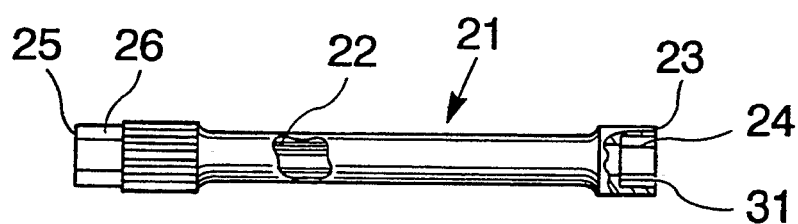
FIG. 4 is an elevational view of the nut starter socket portion of the assembly.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, the goal is to easily position and tighten a nut to fix a connector member of a spinal fixation system between the nut and a seat integral with and located intermediate the ends of a bone bolt. The tool assembly includes nut starter shaft 11 which is ten inches long, for example, and is a conventional ¼ inch square drive post 12 with a spring loaded detent ball 13 therein. At the other end is a 3.5 mm hex drive post 14 for reception in a tool receiving socket at an upper end of a bone bolt 36 shown more specifically in FIG. 7. About 2 inches from the right-hand end of shaft 11, on portion 15 of the shaft, there is a screw thread 16 comprising three turns of ¼-28 UNF thread. This is for temporary storage of the nut which is to be applied to the bone bolt during the surgical procedure.

A shoulder 17 is located about three inches from the right-hand end of the shaft. To the left of this is a cylindrical guide portion 18 which is nominally ¼ inch diameter, and extends to the shoulder 19.

Figure 5:
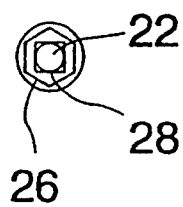
FIG. 5 is a left-hand end view thereof.
Figure 6:
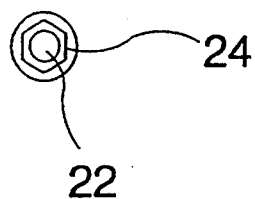
FIG. 6 is a right-hand end view thereof.

The nut starter sleeve 21, which is five inches long, for example, has an internal guide bore 22 extending through it and nominally ¼ inch diameter for a sliding, guiding fit on the guide portion 18 of the shaft. At the right-hand end 23 of the sleeve there is a nominally ⅜ inch hexagonal socket 24 for reception on the nut that is to be secured to the bone bolt. At the left-hand end of the sleeve there is an external hexagonal tool receiving surface 26 for reception of a 7/16 inch socket or adapter thereon. It has a ¼ inch square drive socket 28 (FIG. 5). A straight knurled surface 29 is provided adjacent the left-hand end of the sleeve 21. The overall length of the socket sleeve 21 from the right-hand end 23 to the left-hand end 25 is about 5 inches. The depth of the socket 24 from the right-hand end 23 to the bottom of the socket at 31 is about 0.312 inches.

As indicated above, the sleeve and shaft are assembled together. For this purpose, the sleeve is mounted on the shaft by advancing the sleeve from the right-hand end of the shaft onto the shaft toward the shoulder 19. While doing so, the bore 22 of the sleeve pilots on the guide surface 18 of the shaft, thereby establishing coaxial relationship of the various features of the sleeve with those of the shaft on the axis 32. Then, and referring to FIG. 7, a nut 33 is installed on the thread 16. This nut is intended for installation on the machine screw threads 34 at the upper end of the bone bolt 36 to tighten a connector member 37 on the intermediate seat 38 of the bolt 36.

Figure 7:
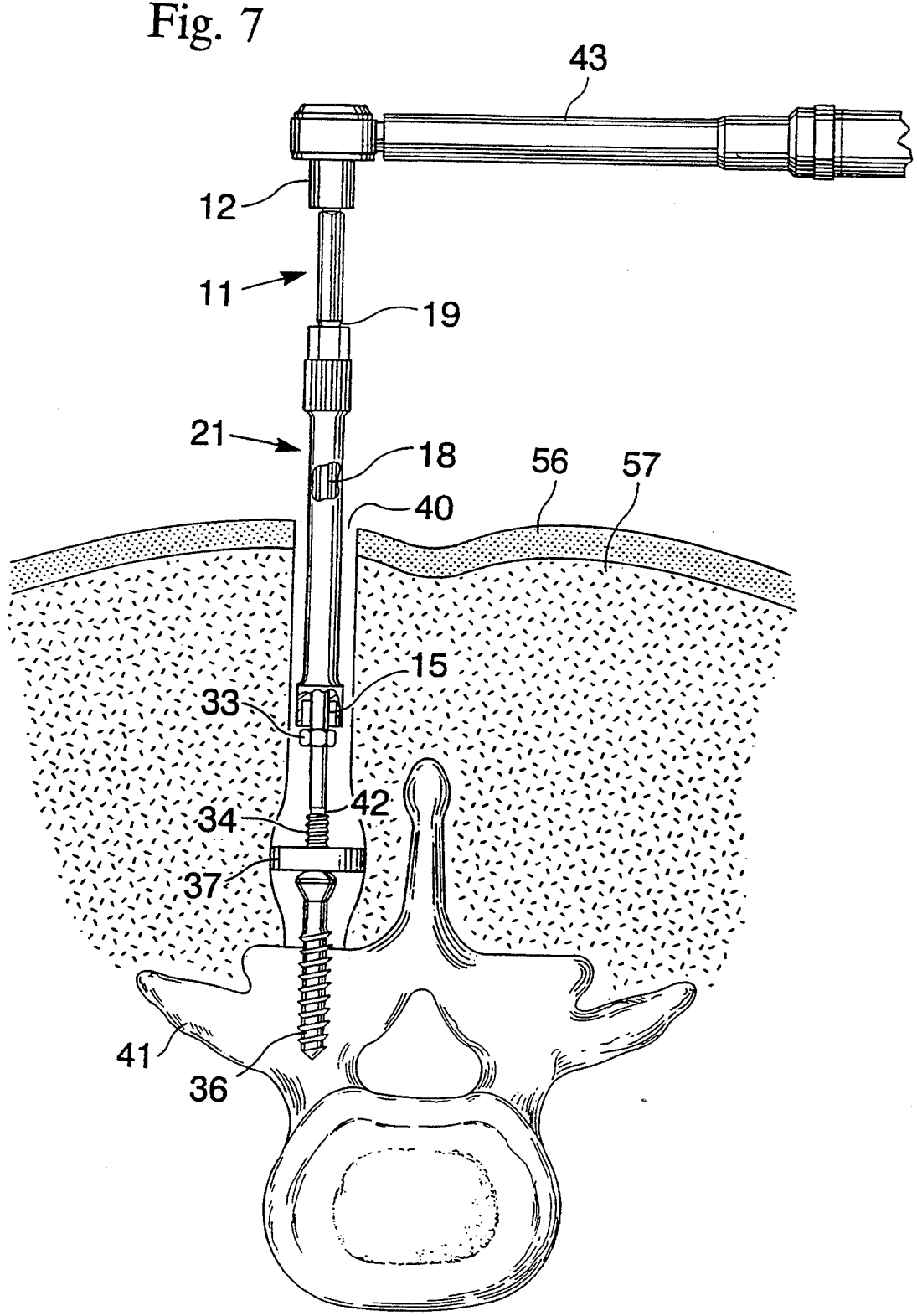
FIG. 7 is an illustration of the assembly in place for installing a bone bolt in a spinal process, particularly the pedicle.
Figure 8:
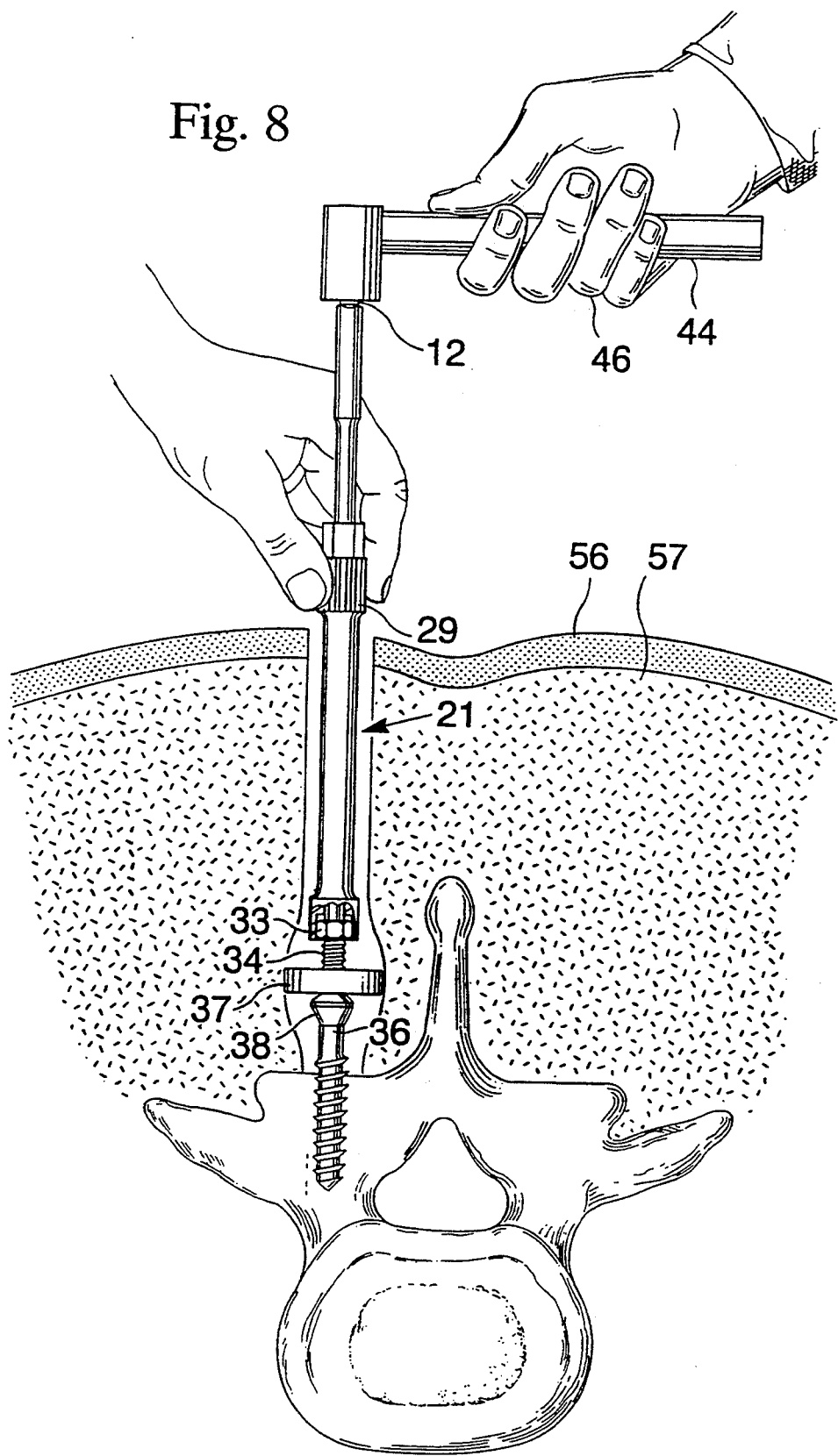
FIG. 8 is an illustration similar to FIG. 7 and in which the nut is being started onto the bolt.

As shown generally in FIG. 7, after making an incision 40, the bone screw end of the bone bolt 36 was installed in the spinal pedicle 41. With the connector member 37 resting on the seat 38 on the bolt, and with the nut and sleeve on the shaft 11, the right-hand end post 14 of the shaft is placed in the mating socket 42 at the upper end of the bolt 36. If desired, a torque wrench 43 can be coupled to the drive post 12 at the upper end of the shaft to be certain that the bolt 36 has been tightened in the pedicle to a desired minimum level of torque. Of course, this extra step may be omitted, if the surgeon desires. Then, a handle 44 is attached to the drive post 12 at the upper end of the shaft and held with the one hand 46 of the surgeon (FIG. 8). Then the knurled portion 29 of the sleeve 21 is gripped between the thumb and forefinger of the other hand of the surgeon to push the sleeve downward on the shaft and securely engage socket 24 thereof onto the nut 33. During the above mentioned installation of the shaft onto the bolt 36, alignment is established between the axis 32 of the shaft and the axis 47 of the bone bolt. Automatically, therefore, the axis of the nut 33 is aligned with tile axis of the machine screw thread 34 on the bolt. Then, the surgeon verifies that the nut, while still on thread 16 of the shaft, is received completely in the socket 24 at the lower end of the sleeve and thereupon rotates the sleeve to turn the nut off the thread 16 and advance the nut downward onto the thread 34, and continues to turn the sleeve until the nut is snug against member 37 while holding the handle 44 with the other hand 46 to prevent turning of the bolt 36.

Figure 9:
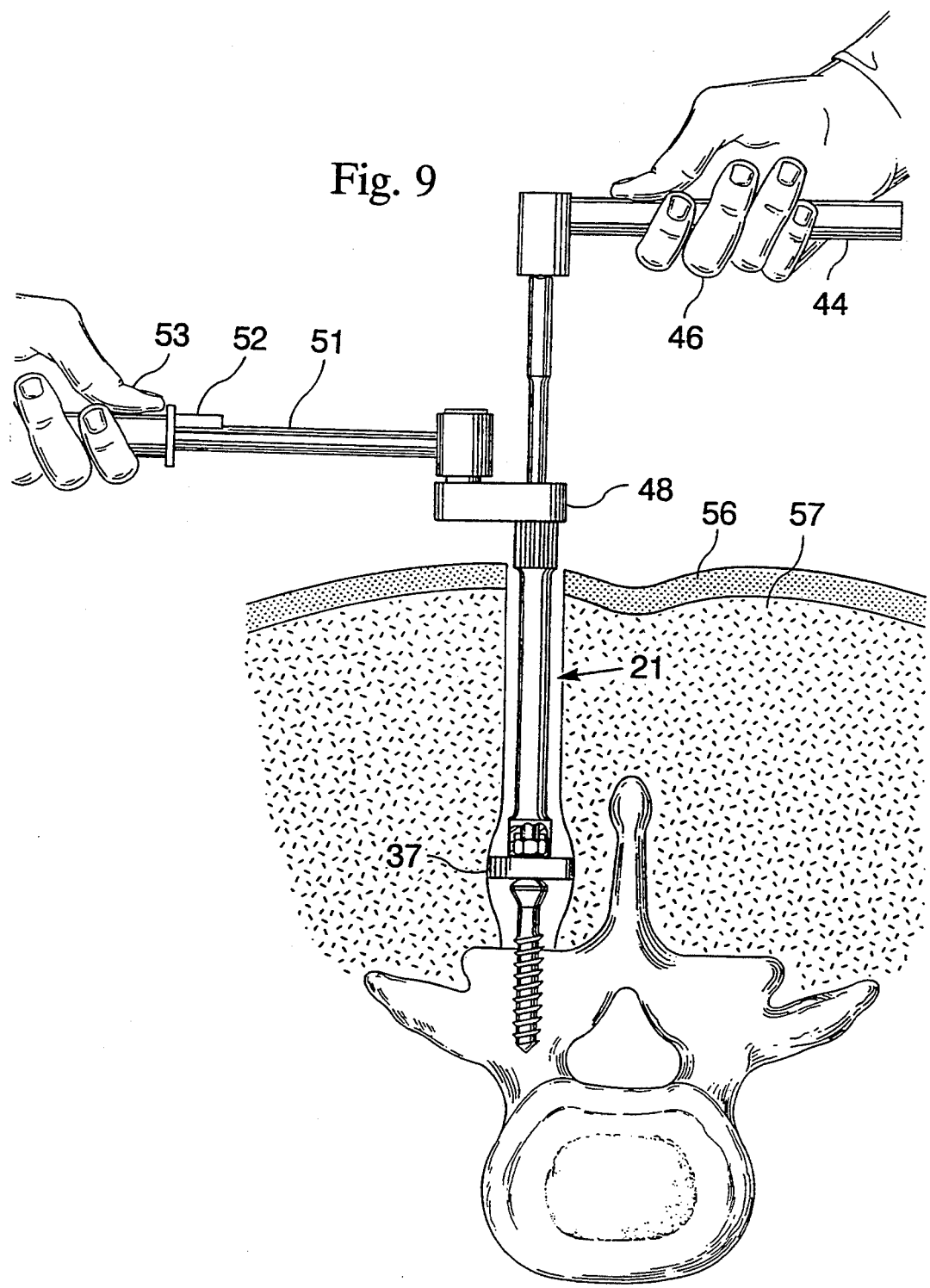
FIG. 9 is all illustration similar to FIG. 8 and where the nut is being torqued onto the bolt.

After the nut is snug against connector member 37, the surgeon can mount the adapter 48 (FIG. 9) on the hexagonal tool receiver surface 26 on the upper end of the sleeve 21 and mount a torque wrench 51 to the adapter and thereupon, while still holding the handle 44 with the one hand, tighten the nut onto the bolt and member 37 to the desired torque shown on the torque wrench indicator 52 as the wrench is pulled by the other hand 53 of the surgeon. This whole procedure of shaft placement, nut installation and torquing can be accomplished with the surgeon's hands well outside the patient's skin 56. It avoids fumbling with small nuts and prevents them from being inadvertently dropped into the spinal anatomy. After this is done, the whole assembly may be removed from the nut and bolt and used at another site.

If desired, the socket 24 can be made deeper than the thickness of the nut 33, and a flange or lip can be provided at the lower edge of the nut for engagement by the lower edge of the socket when the nut is received in the socket, so that axial force may be applied to the nut during assembly, regardless of socket depth.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A nut starting tool assembly for driving a nut onto a threaded end of a bone bolt when the bolt is secured in animal bone, comprising:

a shaft having a first end configured for fitting reception on a tool receiving end of a bone bolt, and having an opposite second end configured for rotating said shaft, said shaft further having storage means at an intermediate portion thereof for reception and temporary storage thereon of a nut to be installed on the threaded end of the bone bolt; and a sleeve coaxially disposed on said shaft and having a first end configured for fitting reception on the nut when temporarily stored on the intermediate portion of the shaft, and an opposite second end configured to be manipulated independent of said shaft to move the nut off said storage means and drive the nut onto the threaded end of the bone bolt when the nut is received within said first end.

2. The tool assembly of claim 1 and further comprising:

a knurled surface on the sleeve adjacent the second end to facilitate rotary manipulation of the sleeve.

3. The tool assembly of claim 1 and further comprising:

a tool receiving external surface at said second end of said sleeve and configured for reception thereon of a driving portion of a rotation tool.

4. The tool assembly of claim 3 and further comprising:

a socket at the second end of the sleeve and configured for reception therein of a driving post of a torque applying tool.

5. The tool assembly of claim 3 and wherein:

the configuration of said first end of said shaft is a 3.5 mm hexagonal drive post;

the configuration of said second end of said shaft is a ¼ inch square drive post; and the configuration of said first end of said sleeve is a ⅜ inch hexagonal socket.

6. The tool assembly of claim 5 and wherein:

the configuration of said external surface at said second end of said sleeve is a hexagonal post.

7. The tool assembly of claim 6 and further comprising: a ¼ inch square socket at the second end of the sleeve.

8. The tool assembly of claim 7 and wherein:

the overall length of said shaft is about 10 inches;

the overall length of said sleeve is about 5 inches; and said storage means at said includes said intermediate portion being threaded at about 2 inches from said first end for threaded reception of the nut thereon.

9. The tool assembly of claim 8 and wherein:

there are about three thread turns at the intermediate portion.

10. The tool assembly of claim 3 and wherein:
said sleeve is guidedly received on said shaft so that the first end of said sleeve is centered on a common axis with the first end of said shaft.

11. The tool assembly of claim 1 and wherein:
said sleeve has an overall length less than the overall length of said shaft.

12. A method of installing a nut on a bolt situated in animal soft tissue and secured in animal bone, the method comprising the steps of:
installing a nut drive sleeve in a bolt holder shaft;
installing a nut on the shaft intermediate between the ends of the shaft;
advancing the bolt holder shaft with sleeve thereon through the adjacent tissue and engaging the bolt holder on the bolt;
engaging the nut with the sleeve;
disengaging the nut from the shaft; and
driving the nut along the shaft with the sleeve while guiding the sleeve on the shaft and thereby guiding the nut onto the bolt.

13. The method of claim 12 and further comprising the step of:
holding the shaft with its axis colinear with the bolt axis while holding the bolt with the shaft to control rotational movement of the bolt while the nut is guided onto the bolt.

14. The method of claim 13 and further comprising the step of:
tightening the nut on the bolt with a torque wrench coupled to a tool receiving external surface on the sleeve.

15. The method of claim 14 and further comprising the step of:
removing the shaft with sleeve thereon from the bolt and adjacent tissue.

16. The method of claim 12 and wherein the step of installing the nut on the shaft comprises:
screwing the nut onto a short thread on the shaft such that the nut will not leave the thread as a result of axial force on the nut relative to the shaft, but only upon application of rotational force on the nut relative to the shaft.

17. The method of claim 12 and wherein the step of engaging the nut with the sleeve comprises:
capturing the nut in a mating drive socket in the sleeve.

18. The method of claim 12 and turning the bolt to tighten the bolt in the bone.

19. The method of claim 18 and further comprising the step of:
holding the shaft with its axis colinear with the bolt axis while holding the bolt with the shaft to control rotational movement of the bolt while the nut is guided onto the bolt.

* * * * *